(12) United States Patent
Yu

(10) Patent No.: US 10,400,201 B2
(45) Date of Patent: Sep. 3, 2019

(54) METHOD AND STRUCTURE FOR COMPREHENSIVE UTILIZATION OF CO-PRODUCTS OF ALCOHOL PRODUCTION FROM GRAINS

(71) Applicant: KIWI GREEN TECHNOLOGIES, LLC, Roseville, CA (US)

(72) Inventor: Guo Yu, Roseville, CA (US)

( * ) Notice: Subject to any disclaimer, the term of this patent is extended or adjusted under 35 U.S.C. 154(b) by 0 days.

(21) Appl. No.: 15/675,312

(22) Filed: Aug. 11, 2017

(65) Prior Publication Data

US 2018/0051239 A1   Feb. 22, 2018

Related U.S. Application Data

(60) Provisional application No. 62/377,376, filed on Aug. 19, 2016.

(51) Int. Cl.

| | |
|---|---|
| *C12F 3/02* | (2006.01) |
| *C12P 5/02* | (2006.01) |
| *C12N 1/12* | (2006.01) |
| *C12M 1/00* | (2006.01) |
| *C10L 1/02* | (2006.01) |
| *A23K 10/38* | (2016.01) |
| *C12M 1/107* | (2006.01) |
| *C10L 3/08* | (2006.01) |

(52) U.S. Cl.
CPC ............ *C12F 3/02* (2013.01); *A23K 10/38* (2016.05); *C10L 1/026* (2013.01); *C10L 3/08* (2013.01); *C12M 21/04* (2013.01); *C12M 43/00* (2013.01); *C12M 43/06* (2013.01); *C12N 1/12* (2013.01); *C12P 5/023* (2013.01); *C10L 2200/0469* (2013.01); *C10L 2290/26* (2013.01); *C10L 2290/54* (2013.01); *Y02E 50/343* (2013.01)

(58) Field of Classification Search
None
See application file for complete search history.

(56) References Cited

U.S. PATENT DOCUMENTS

| | | |
|---|---|---|
| 4,035,517 A | 7/1977 | Magny et al. |
| 5,135,765 A | 8/1992 | Kishi et al. |
| 6,024,877 A | 2/2000 | Bonnet et al. |
| 7,670,633 B2 | 3/2010 | Srinivasan et al. |
| 8,153,006 B1 | 4/2012 | Fessler et al. |
| 8,481,295 B2 | 7/2013 | Van Leeuwen et al. |
| 8,835,665 B2 | 9/2014 | Reaney et al. |
| 8,969,605 B2 | 3/2015 | Bosetti et al. |
| 9,051,538 B1 | 6/2015 | Roa-Espinosa |
| 9,068,139 B2 | 6/2015 | Woyewoda et al. |
| 9,113,645 B2 | 8/2015 | Bruinsma et al. |
| 9,138,660 B2 | 9/2015 | Yamamoto |
| 9,161,554 B1 | 10/2015 | Darling et al. |
| 2013/0236936 A1 | 9/2013 | Lee |
| 2014/0147897 A1 | 5/2014 | Lee |
| 2015/0305370 A1* | 10/2015 | Bleyer ................ A23K 10/38 435/71.2 |

FOREIGN PATENT DOCUMENTS

WO   WO-2010/138110 A1 * 12/2010

OTHER PUBLICATIONS

J. W. Schroeder (Distillers grains as a protein and energy supplement for dairy cattle, North Dakota State University (2003), AS-1241, p. 1-8).*

Prosonix, Ethanol Jet cooking, p. 1, Dec. 10, 2010.*

\* cited by examiner

*Primary Examiner* — Iqbal H Chowdhury
(74) *Attorney, Agent, or Firm* — Lei Jiang

(57) ABSTRACT

A method is provided for treating distiller's grains with solubles (DGS) to produce one or more byproducts. The method includes separating the DGS into a low protein mixture and a high protein mixture. The method includes generating, from the low protein mixture, a biogas by an anaerobic digestion process. The method includes generating, from the high protein mixture, at least one of a vegetable oil from a vegetable oil separation process, a high protein animal feed from a separation process and a microalgae biomass material from a microalgae production process.

11 Claims, 6 Drawing Sheets

METHOD AND STRUCTURE FOR COMPREHENSIVE UTILIZATION OF CO-PRODUCTS OF ALCOHOL PRODUCTION FROM GRAINS

CROSS-REFERENCE TO RELATED APPLICATIONS

This application claims priority to and the benefit of U.S. Provisional Patent Application No. 62/377,376 that was filed on Aug. 19, 2016, the entire disclosure of which is herein incorporated by reference.

BACKGROUND

The present application relates to a method and structure for utilizing co-products of alcohol production. It finds particular applications in the field of making use of co-products of alcohol production from grains.

This application is related to the area of co-produced material utilization in alcohol production and provides a method for comprehensively making use of co-products of alcohol production from grains. This application can be used in association with co-product materials from various types of alcohol production, including, but not limited to, liquor, wine, rice wine, beer, and ethanol.

Depending on different processing procedures, a variety of co-products can be produced from alcohol production from grains. These co-products include, but are not limited to, whole stillage, thin stillage, wet distiller's grains (WDG), dry distiller's grains (DDG), syrup, wet distiller's grains and solubles (WDGS), dry distiller's grains and solubles (DDGS), condensed distiller's solubles (CDS). It will be appreciated that, as used herein, the term DGS (distiller's grains with solubles) may be used to represent the various co-products mentioned above. DGS also covers all other generally used terms for alcohol production industry, such as spent grains.

DGS, especially the ones with low protein and lipid contents, may be a potential source of pollution, if not treated appropriately. For example, WDG, due to its high moisture content, may have a life time of as short as four to five days and can easily spoil and release hazardous substances.

Currently a typical use of DGS is as animal feed. However, without concentration or removal of other non-protein portions, the typical protein content of DGS may be relatively low. In an example, the protein content in DGS may be less than or equal to about 30%. In another example, the DGS protein content may be less than or equal to about 20% from certain liquor production processes. Also, additional amino acids may need to be added if such DGS is used as animal feed. In some examples, high protein and high amino acid containing animal feed has a higher value than normal or low protein animal feed. In this way, as protein and/or amino acid concentrations increase within the animal feed, the price of the animal feed may likewise increase.

In addition, using the co-products only as animal feed has the drawback of being susceptible to market fluctuation. For example, making renewable energy or other products (e.g. biogas/bio-oil/algae) from these alcohol production co-products may potentially generate more revenue, save cost, and/or generate economic feasibility for the producer.

SUMMARY

Aspects of the present application address the above matters, and others. According to one aspect, a method for treating distiller's grains with solubles (DGS) to produce one or more byproducts is provided. The method comprises separating the DGS into a low protein mixture and a high protein mixture. The method further comprises processing the low protein mixture to generate biogas, or generate heat via drying and combustion, or to generate animal bedding material, or for other use. The method further comprises generating, from the high protein mixture, at least one of a vegetable oil from an oil separation process, a high protein animal feed from a liquid/solid separation process, and a microalgae biomass material from a microalgae production process.

According to another aspect, an integrated modular facility for treating distiller's grains with solubles (DGS) to produce one or more byproducts is provided. The integrated modular facility comprises an animal feed production module, wherein the animal feed production module is configured to separate the DGS into a low protein mixture and a high protein mixture. The integrated modular facility comprises a high fiber processing module, wherein the high fiber processing module is configured to generate, from the low protein mixture, a biogas. The integrated modular facility comprises a bio-oil recovery module, wherein the bio-oil recovery module is configured to generate, from the high protein mixture, at least one of a vegetable oil, a high protein animal feed, or a microalgae biomass material.

According to another aspect, a method for treating distiller's grains with solubles (DGS) to produce one or more byproducts is provided. The method comprises separating the DGS into a low protein mixture and a high protein mixture. The method further comprises generating biogas from the low protein mixture. The method further comprises generating, from the high protein mixture, a bio-oil mixture and a high protein animal feed.

Those of ordinary skill in the art will appreciate still other aspects of the present application upon reading and understanding the appended description.

FIGURES

The application is illustrated by way of example and not limitation in the figures of the accompanying drawings, in which like references generally indicate similar elements and in which.

DESCRIPTION

Figure 1:
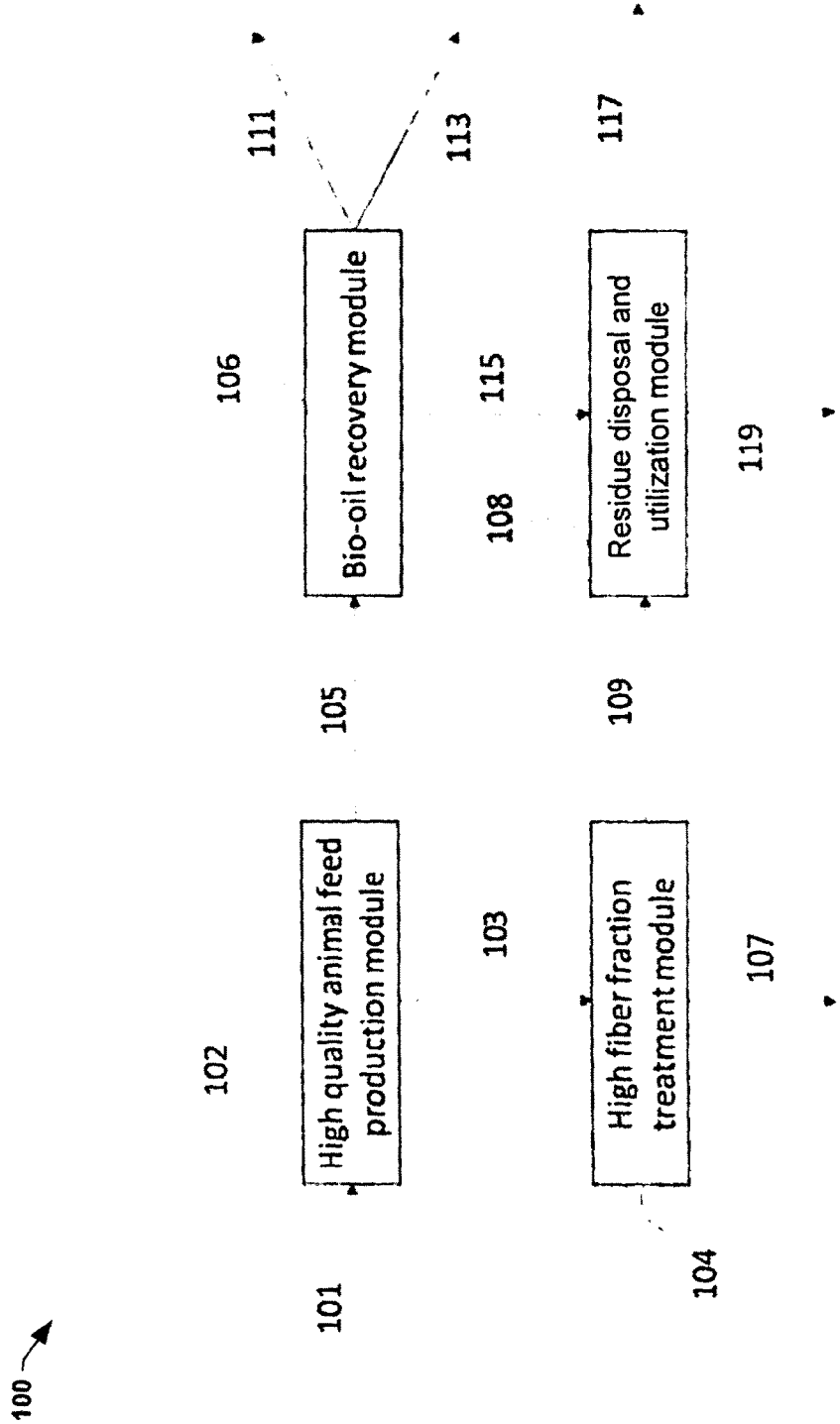
FIG. 1 illustrates an example method for treating distiller's grains with solubles (DGS) to produce one or more byproducts.

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

FIG. 1 is a schematic illustration of a Method 100 for treating distiller's grains with solubles (DGS) to produce one or more byproducts. The Method 100 can provide an integrated, modular system for processing the co-products of alcohol production. The integrated, modular system of the Method 100 can comprise one or more modules (e.g., 102, 104, 106, 108 and/or 202, 204, 206, 208) for treating DGS to produce one or more byproducts. The Method 100 comprises a feedstock stream 101 (e.g., a DGS feedstock stream), which can comprise co-product streams from a number of different alcohol production processes including, but not limited to, whole stillage, thin stillage, wet distiller's grains (WDG), dry distiller's grains (DDG), syrup, wet distiller's grains and solubles (WDGS), dry distiller's grains and solubles (DDGS), condensed distiller's solubles (CDS). In an example, the DGS can have a moisture content that is greater than or equal to 80%. However, if the moisture content of the DGS is less than or equal to 80%, liquid (e.g., water) can be added to the DGS to raise the moisture content to 80% or greater.

In an example, the Method 100 comprises a high protein animal feed production module 102, a low protein, higher fiber portion processing module 104, a bio-oil recovery module 106, and a residue disposal and utilization module 108. Table 1 illustrates an example of a composition of a co-product from an alcohol production process that uses sorghum and wheat as major feedstock. In an example, separating the DGS may comprise at least one of anaerobic digestion and drying for combustion.

TABLE 1

Composition of the co-product from a liquor production using sorghum and wheat as the major feedstock

|  | Value | Unit |
| --- | --- | --- |
| Moisture | 12.8 | % |
| Ash | 8.9 | % TS |
| Crude Protein | 22.9 | % TS |
| Crude Fat | 4.3 | % TS |
| Acid detergent fiber (ADF) | 39.2 | % TS |
| Neutral detergent fiber (NDF) | 42.6 | % TS |
| Arginine | 0.56 | % TS |
| Histidine | 0.31 | % TS |
| Isoleucine | 0.84 | % TS |
| Leucine | 1.65 | % TS |
| Lysine (total) | 0.31 | % TS |
| Methionine | 0.30 | % TS |
| Phenylalanine | 0.83 | % TS |
| Threonine | 0.80 | % TS |
| Tryptophan | 0.09 | % TS |
| Valine | 1.10 | % TS |
| Alanine | 1.34 | % TS |
| Aspartic acid | 1.01 | % TS |
| Cystine | 0.38 | % TS |
| Glutamic acid | 4.76 | % TS |
| Glycine | 0.81 | % TS |
| Proline | 1.72 | % TS |
| Serine | 0.93 | % TS |
| Tyrosine | 0.63 | % TS |
| Net Energy (lactation) | 0.73 | Mcal/lbs |
| Net Energy (maint.) | 0.74 | Mcal/lbs |

TABLE 1-continued

Composition of the co-product from a liquor production using sorghum and wheat as the major feedstock

|  | Value | Unit |
| --- | --- | --- |
| Net Energy (gain) | 0.48 | Mcal/lbs |
| Digestable Energy | 1.40 | Mcal/lbs |
| Metablizable Energy | 1.28 | Mcal/lbs |

Referring to the high protein animal feed production module 102, in an example, the majority of the protein portion and a significant portion of bio-oil in DGS may be concentrated in a liquid stream. This liquid stream may be separated from a solid, high-fiber, low protein stream 103 (e.g., a high-fiber, low protein solid fraction stream 103) via different separation processes. In an example, these separation processes may include, but are not limited to, centrifuging, filtration, and/or pressing. The high protein animal feed production module 102 can generate the high-fiber, low protein stream 103 and a high protein, liquid fraction stream 105.

Referring to the low protein, higher fiber portion processing module 104, a number of different processing methods can be used to treat the high-fiber, low protein stream 103. Possible treatment methods comprise treating in anaerobic digester, drying to make animal bedding, used for combined heat and power production, land application, landfilling, etc. In an example, the low protein, higher fiber portion processing module 104 can produce, from the low protein stream 103, a biogas stream 107 and a nutrient stream 109. In an example, the biogas stream 107 can comprise between about 40% to about 70% methane, and between about 30% to about 50% carbon dioxide.

Referring to the bio-oil recovery module 106, a bio-oil stream 111 may be recovered via methods including, but not limited to, centrifuging, extraction, membrane filtration, and gravity separation. Then a high protein, high value animal feed stream 113 may be produced via solid/liquid separation. In an example, the solid/liquid separation methods include, but are not limited to centrifuging, filtration, and pressing. The bio-oil recovery module 106 may produce a stream 115 (e.g., a liquid stream after high protein content removal). In an example, the stream 115 is a de-oiled, low protein stream, consisting of mainly water, some soluble compounds such as saccharides, and nutritional elements such as phosphorous. Referring to the residue disposal and utilization module 108, the stream 115 from the bio-oil recovery module 106 and the stream 109 from the low protein, higher fiber portion processing module 104 can be used to produce an algal biomass stream 119, which may be used as feedstock for biofuel production, or other animal feed production. A liquid residue stream 117 may also be produced by the residue disposal and utilization module 108.

Figure 2:
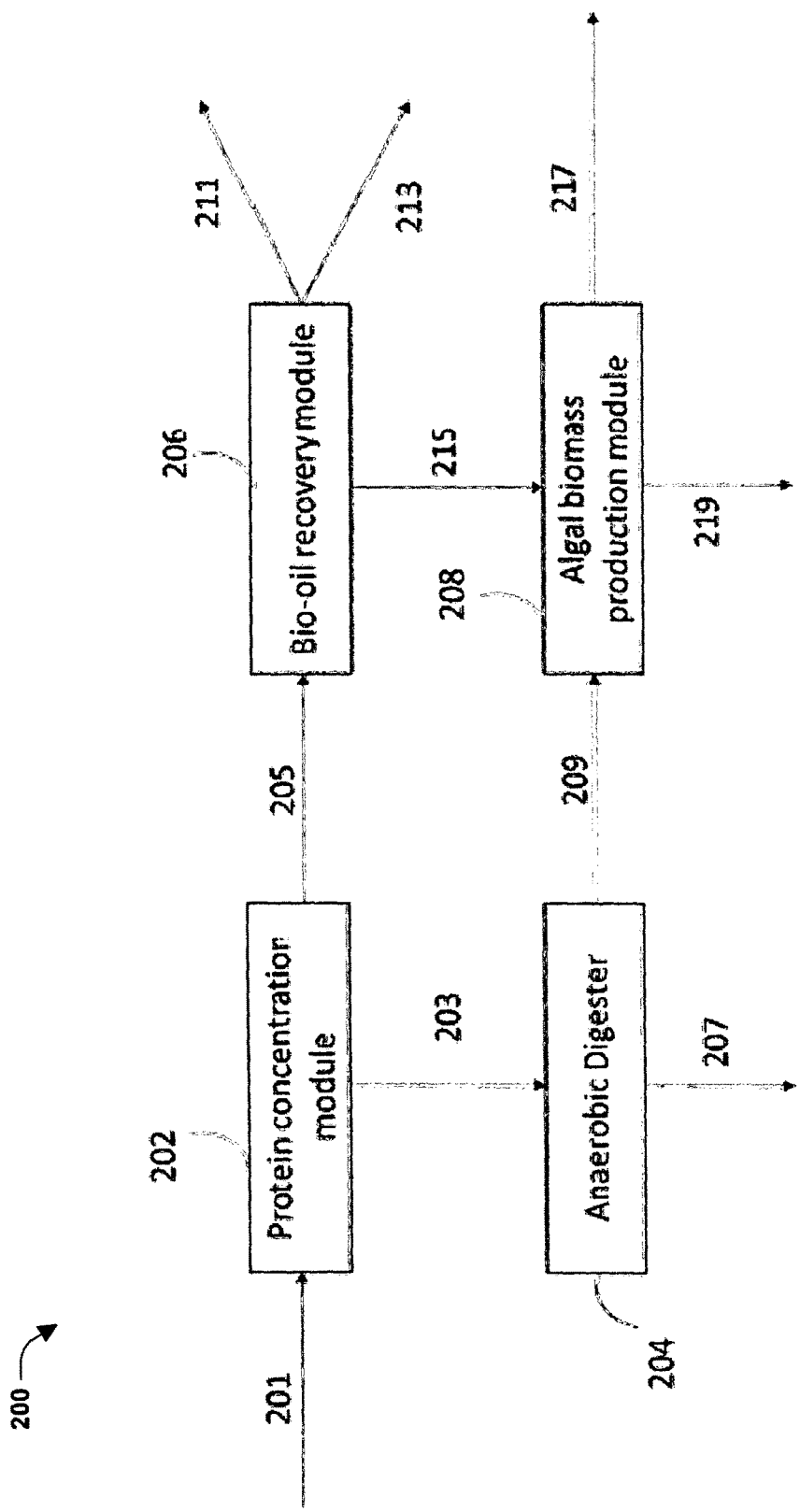
FIG. 2 illustrates an example method of FIG. 1 for treating distiller's grains with solubles (DGS) to produce one or more byproducts.

FIG. 2 is a schematic illustration of a Method 200 for treating DGS to produce one or more byproducts. The Method 200 can provide an integrated, modular system for processing the co-products of alcohol. The Method 200 may share one or more steps with the method 100 described above and illustrated in FIG. 1. The Method 200 comprises a protein concentration module 202, an anaerobic digester module 204, a bio-oil recovery module 206, and an algal biomass production module 208.

It will be appreciated that FIG. 1 illustrates an example method 100 of an overall process for treating distiller's grains with solubles (DGS) to produce one or more byproducts. FIG. 2 illustrates an example Method 200 of carrying out the Method 100 of FIG. 1. For example, step 202 of FIG. 2 is an example method of step 102 of FIG. 1. Likewise, step 204 of FIG. 2 is an example method of step 104 of FIG. 1. Similarly, step 206 of FIG. 2 is an example method of step 106 of FIG. 1. Further, in an example, the algal biomass production module 208 of FIG. 2 is an example method 108 of FIG. 1.

The Method 200 comprises a feedstock stream 201, which can comprise co-product streams from a number of different alcohol production processes including, but not limited to, whole stillage, thin stillage, wet distiller's grains (WDG), dry distiller's grains (DDG), syrup, wet distiller's grains and solubles (WDGS), dry distiller's grains and solubles (DDGS), and condensed distiller's solubles (CDS).

Referring to the protein concentration module 202, in an example, the majority of the protein portion and a significant portion of bio-oil in DGS may be concentrated in a liquid stream 205. This liquid stream 205 may be separated from the solid, high-fiber, low-protein stream 203 via different separation processes. The separation processes include, but are not limited to, centrifuging, filtration, and pressing. In an example, the protein concentration module 202 may comprise a size reduction process, a steeping process, and/or a sieve separation to generate a high-protein stream 205 and a solid, high-fiber, low protein stream 203. In an example, the order of separating may comprise steeping, followed by size reduction, followed by separating the liquids and solids. In another example, the order of separating may comprise size reduction, then steeping, and followed by separating of liquids and solids.

The chemicals that are used during the steeping may comprise at least one of sodium hydroxide, potassium hydroxide, sodium sulfite, sodium sulfate, sodium metabisulfite, sodium bisulfite, and sodium dodecyl. In an example, the enzymatic solutions used during the steeping comprise at least one of protease, carbohydrase, cellulase, hemicellulase, ligninase and pectinase. The steeping can have a steeping time that is between about 1 hour to about 48 hours at a temperature that is between about 25 Celsius to about 85 Celsius. In an example, the size reduction may comprise at least one of disk milling, roller milling, hammer milling, colloid milling, and press milling. The separating may comprise using a sieve that has one or more pores with a pore size that is between about 0.1 micrometer to about 5 millimeters.

The Method 200 comprises a bio-oil recovery module 206 that is substantially similar to the bio-oil recovery module 106 of FIG. 1. The bio-oil recovery module 206 can generate a bio-oil stream 211 that is similar to the bio-oil stream 111 of FIG. 1 and a high protein, high value animal feed stream 213 that is similar to the high protein, high value animal feed stream 113 of FIG. 1.

Similar to the example of FIG. 1, the algal biomass production module 208 may produce an algal biomass stream 219 and a liquid residue stream 217 that are similar to the algal biomass stream 119 and a liquid residue stream 117 generated in FIG. 1.

Figure 3:
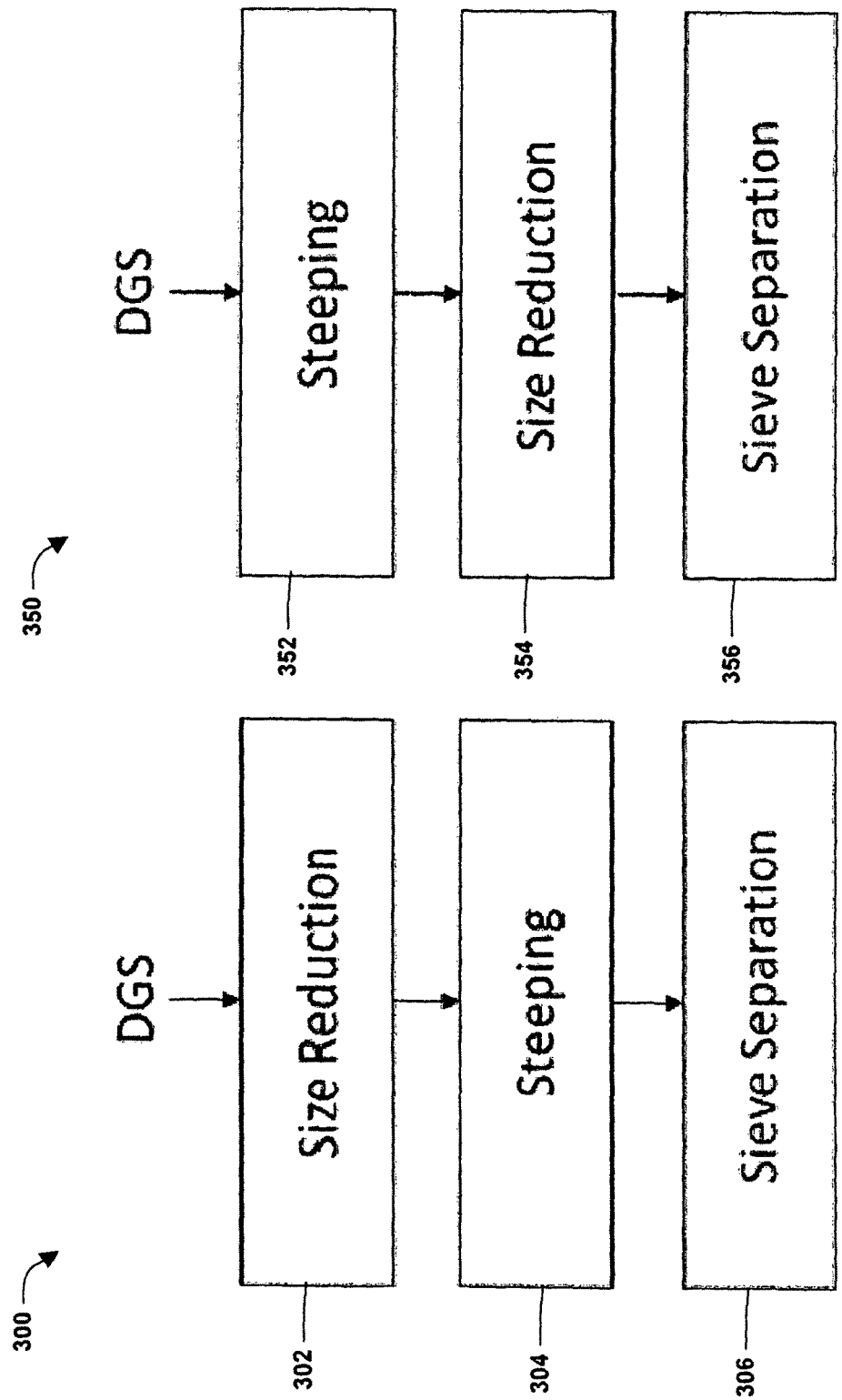
FIG. 3A illustrates an example method for treating distiller's grains with solubles (DGS) to produce one or more byproducts.
FIG. 3B illustrates an example method for treating distiller's grains with solubles (DGS) to produce one or more byproducts.

FIGS. 3A and 3B illustrate two different concentration processes for the protein concentration module 202 of FIG. 2. It will be appreciated that FIGS. 3A and 3B are refinements of the process illustrated in FIG. 2. FIG. 3A illustrates a concentration process 300 in which size reduction 302 occurs first, followed by steeping 304 of the sized reduced DGS, and lastly a sieve separation 306. During the steeping step, protein matrix in DGS is broken down by chemicals/enzymes into small protein segments; while fiber matrix remains intact. The size reduction prior to the steeping step improves surface area of DGS, thereby improving the steeping efficiency. Therefore, the protein separation can be improved by adding the size reduction step. In the last, the size of the sieve can be controlled to remove the large fibers from the small and soluble protein segments. On the other hand, the size reduction step can also be operated after the steeping step. FIG. 3B illustrates a concentration process 350 in which steeping 352 occurs first, followed by size reduction 354, and lastly a sieve separation 356. After steeping, DGS samples are softer and easier to grind, which can potentially reduce the energy consumption in the size reduction step. It will be appreciated that the parameters of the sieve separation 356 and the solid/liquid separation in FIG. 3B may be substantially similar to the sieve separation 306 and the solid/liquid separation in FIG. 3A. In an example, it is noted that the processes FIGS. 3A and 3B may also include other additional steps beyond steeping, size reduction, and sieve separation. After sieve separation, dewatering steps can be added to reduce the water content of the separated high-protein portion and high-fiber portion. Technologies used in the dewatering step include but not limited to filtration, centrifugation, settling, and different types of drying.

In FIG. 3A, in an example, the size reduction 302 may be selected from at least one of disk milling, roller milling, hammer milling, colloid milling, and/or press milling. In an example, the steeping 304 may be conducted by immersing the size reduced DGS in chemicals (including water) and/or enzyme solutions. The chemical solution may be prepared by mixing water with one or more chemicals. The chemicals may comprise sodium hydroxide, potassium hydroxide, sodium sulfite, sodium sulfate, sodium metabisulfite, sodium bisulfite, and sodium dodecyl. The enzymatic solution includes, but not limited to, protease, carbohydrase, cellulase, hemicellulase, ligninase, and pectinase. The concentration of chemical or enzymatic solutions is 0.001% to 50%. DGS is typically steeped for a period of time of 1 hour to 48 hours at a temperature of 25° C. to 85° C.

Next, the steeped DGS may be separated by the sieve separation step 306 to produce the high-protein portion (e.g., 105 or 205) and a high-fiber portion (e.g., 103 or 203). The retentate of the sieve separation step 306 may be collected as a high-fiber portion and the filtrate may be collected as a high-protein portion. In an example, the pore size of the sieve may be about 0.1 micrometers to about 5 millimeters. The separated high-fiber portion can be used, but is not limited to, feedstock for anaerobic digestion (e.g., at 104 in FIG. 1 or 204 in FIG. 2).

In an example, the high-protein portion may be further treated with solid/liquid separation to produce solid protein. This process can happen after bio-oil recovery if bio-oil recovery process is installed. The solid/liquid separation may be realized by selecting at least one of centrifugation, membrane filtration, and sedimentation. The separated waste liquid can be recycled to the steeping step.

Referring to FIG. 3B, the concentration process 350 can produce protein and fiber enriched materials from DGS. In this example, the DGS can be steeped 352 prior to size reduction 354. The size reduced DGS may be subjected to the sieve separation step 356 to produce the high-protein portion 105, 205 and the high-fiber portion 103, 203. Next, the solid/liquid separation of the high-protein portion 105, 205 and the high-fiber portion 103, 203 can produce the liquid waste and the solid high protein and high fiber materials.

In an example, after harvesting the protein and/or, the stream 103 of FIG. 1 may contain a relatively high percentage of fiber (e.g., 50% to 70%, dry basis) and a lower amount of crude protein (e.g., 5% to 15%). The solid content of the fiber slurry can vary from 5% to 20%. The fiber slurry can be landfilled, composted, dried and then incinerated or anaerobically digested (e.g., at 104, 204).

In an example, the anaerobic digester module 204 comprises any number of different AD systems, such as mesophilic, thermophilic, CSTR, plug flow, and vertical flow. In an example, a solid digester may be generated for treating the high-solid content stream 103 that was generated from the high protein animal feed production module 102. The anaerobic digester module 204 may produce the biogas stream 207 and a digestate stream 209. The biogas stream 207 may contain methane (40-70%), carbon dioxide (30-50%), and other impurities. The biogas stream 207 can be used to provide process heat and/or electricity, or may be further purified and used as feedstock for transportation fuel production or other purposes. The digestate stream 209 may be land applied, composted, and treated in a wastewater treatment plant. In an example, the digestate stream 209 can be used to provide nutrients for the algal biomass production module 208.

Figure 4:
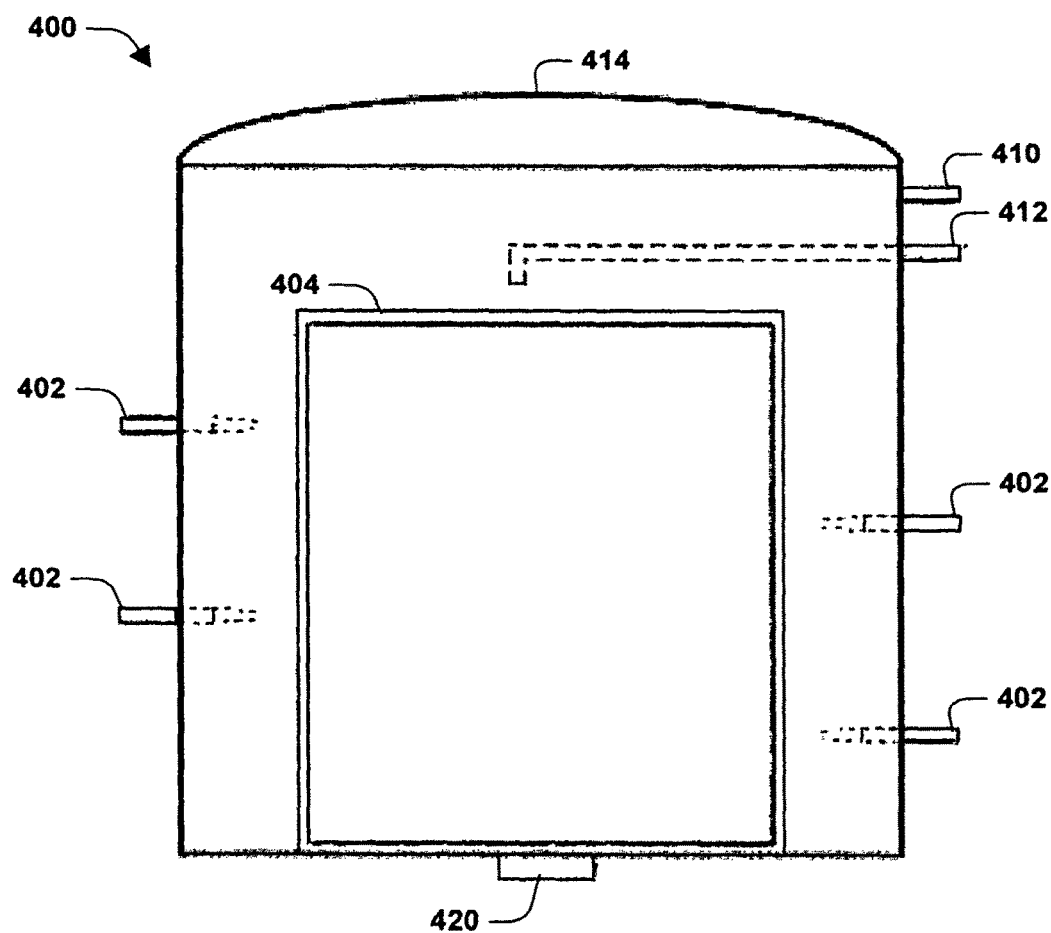
FIG. 4 illustrates a structure for treating distiller's grains with solubles (DGS) to produce one or more byproducts.

FIG. 4 is an example of a digester 400 (e.g., such as the anaerobic digester in FIG. 2). The novel dry anaerobic digester 400 (e.g., illustrated in FIG. 4) may be provided for fiber slurry treatment at a mesophilic condition with a high total solid content. The fiber slurry can have varying total solids content, can be directly put into the digester, or can be dewatered and then loaded in the digester. In this way, this design has the flexibility of handling the fiber slurry with a wide range of total solids content. In other examples, the fiber slurry can be mixed with other waste organics such as activated sludge or food wastes and then co-digested in the system described.

The digester 400 may comprise one or more walls that define openings for injection pies 402. In an example, there may be a total of four injection pipes 402 arranged alongside walls of the digester 400. The digester 400 may comprise a door 404 through which access to an interior of the digester 400 is provided (e.g., the door 404 can be moved between an opened and a closed position). The digester 400 may further comprise a top injection pipe 412 for injecting a material and/or product into the interior of the digester 412. In addition or in the alternative, the injection pipes 402 can likewise receive a material and/or product for injecting into and/or receiving from the digester 400. The digester 400 comprises a gas outlet 410 for venting gas between an exterior of the digester 400 and an interior of the digester 400. A flexible cover 414 may be disposed at a top of the digester 400, such as by being attached to side walls. A collecting trench 420 (e.g., a leachate collecting trench) may be disposed at a bottom of the digester 400, such as along a bottom wall.

The size can be varied with the amount of the processed feedstock (fiber slurry in this case). It can be made of stainless steel or concrete. The retention time can be 20-40 days under 35-40° C. operating temperature and absence of oxygen. The inlets/outlets are limited to these locations to ease feedstock loading and biogas usage.

The fiber slurry stream 203 can be injected into the digester through a side, a top, or both injection pipes. In an example, the side injection pipes can have varying heights that provide even distribution of fiber slurry. In some examples, fiber slurry may be injected before the digestion process begins and the digestate is removed at the end of digestion process. In other examples, extra inoculum can be injected to recover failed digestion process. In this way, the injection pipes can be used for adding both fiber slurry and inoculum. The injection pipes can be connected a vacuum pump that removes digestate from the digester.

In an example, the system may be operated with or without internal agitator(s) during the digestion process. In some examples, leachate may be collected at the leachate collecting trench and may then be recycled to digester through the top injection pipe.

The biogas stream 207 may be stored at a head space of the digester and may be directly used for heat production. In an example, the biogas may be recirculated back to a bottom of the digester before being used. Once the fiber slurry completes a digestion cycle, it may be discharged using an extraction vacuum pump. An air-tight door 404 can be opened to allow for digestate removal and for maintenance purposes.

The stream 205 may comprise the liquid portion which contains a majority of the protein and the bio-oil in the original feedback stream 201. In an example, the bio-oil recovery module 206 can separate the bio-oil (e.g., 211) from the stream 205. DGS may contain between about 3% to about 15% of vegetable oils (dry basis) depending on the type of grains used for alcohol fermentation. In an example, the vegetable oils may be high value products, which can be used as advanced supplements for animal feed and feedstock for biodiesel production.

In an example, the bio-oil can be separated from the permeate by centrifugation with a disk-stack centrifuge or a decanter. In an example, vegetable oil can be separated by a static settling method, in which the permeate was held in a settling tank for a period of time. In an example, when generating products from the high protein mixture, separation may occur by one or more of centrifugation with a disk-stack centrifuge or a decanter.

In an example, pretreatment methods to improve oil separation efficiency in the bio-oil recovery module 106 may be provided. These pretreatment methods may include, but are not limited to: a) heating the permeate to between about 60° C. to about 100° C. to break the oil-water emulsion bond; b) adding demulsifier (e.g., alkali, alcohol, etc.) to the permeate; and/or c) adjusting the pH of the permeate with acids or alkali. By applying the above process, the oil separation efficiency can be between about 20% to about 90%.

After the bio-oil 211 is removed, the high protein, high value animal feed stream 213 and the liquid portion 215 may be separated. In an example, the solid/liquid separation can be achieved by at least one of centrifugation, membrane filtration, and sedimentation. The separated waste/liquid stream 215 can be recycled to the steeping step. In an alternative example, as shown in FIG. 2, the stream 215 can be used for algal biomass production.

In an example, the algal biomass production module 208 can carry out the method for cultivating various microalgae species by using nutrients and carbon sources existing in thin stillage. Microalgae is a promising feedstock for producing next generation biofuels. However, microalgae cultivation faces many challenges, in which low-cost nutrients are crucial because they can significantly lower cultivation cost. Nutrients in thin stillage include, but are not limited to, nitrogen, phosphorous, and various carbon sources like glycerol, glucose and maltose. Under controlled cultivation condition, microalgae can uptake these nutrients and utilize the carbon sources to grow and produce massive algal biomass.

As provided herein, the stream 215 (and, in an example, the stream 209) can be added into a microalgae cultivation medium. The pH of the cultivation medium can be adjusted to the range of between about 6 to about 9. A total nitrogen (TN) may be adjusted to a range of about 10 to about 1200 mg/L. The total phosphorous (TP) may be adjusted to a range of about 1 mg/L to about 200 mg/L. A total organic carbon (TOC) may be adjusted to a range of between about 50 mg/L to about 5000 mg/L. The other cultivation conditions can include: temperature (e.g., between about 15° C. to about 45° C.), light intensity (e.g., between about 3000 Lux to about 12000 Lux), $CO_2$ concentration (e.g., between about 3% to about 35%). Microalgae species that can grow and produce massive algal biomass in such medium described above include but are not limit to: *Chlorella, Spirulina*, rhodophyta, Phaeophyta, diatom, chrysophyceae, *Botryococcus*, stonewort, dinoflagellate, xanthophyta, and etc. The produced algal biomass may be harvested and used for biodiesel production or as animal feed, or for other purposes.

Figure 5:
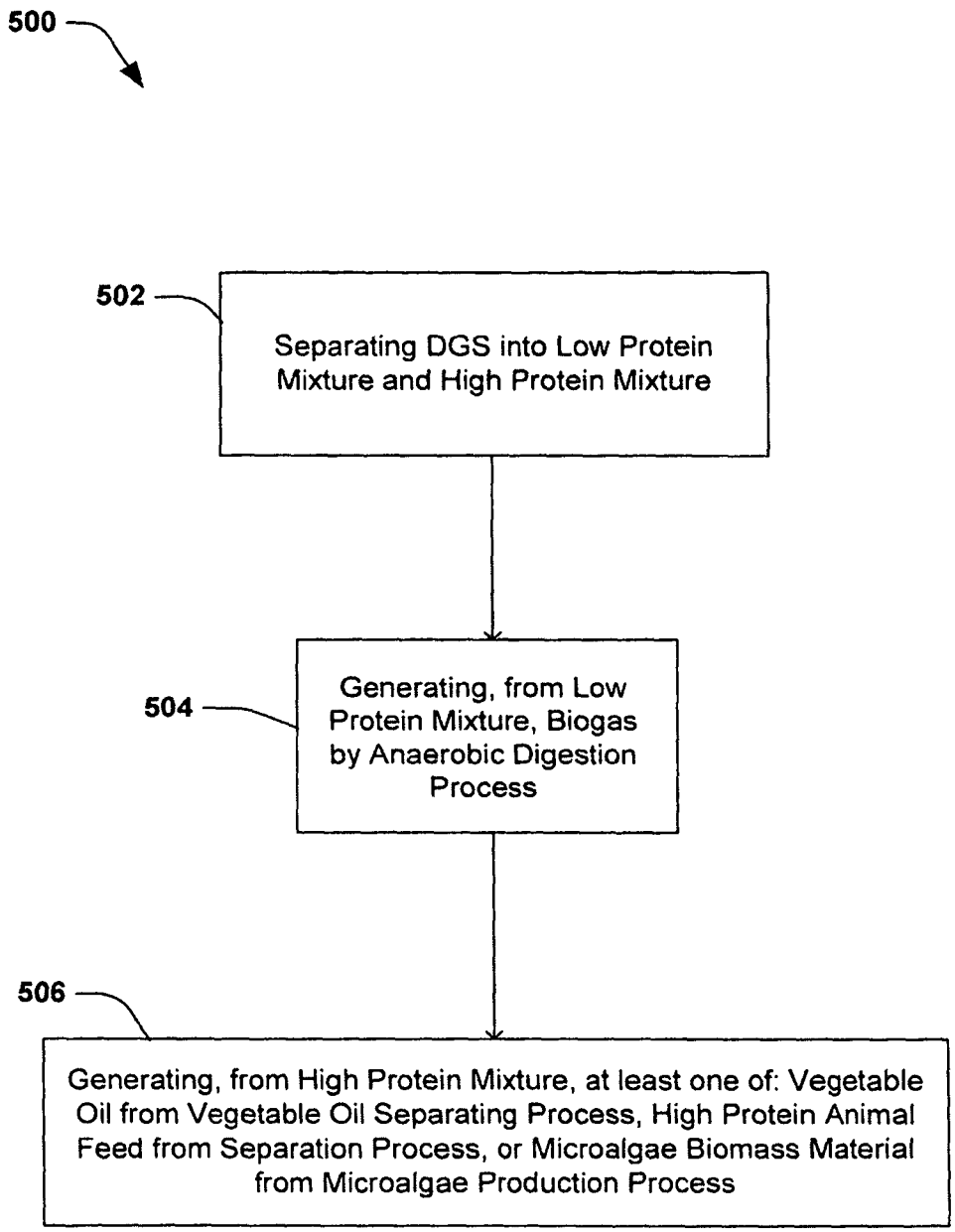
FIG. 5 illustrates an example method for treating DGS to produce one or more byproducts.

Referring to FIG. 5, an example method 500 for treating DGS to produce one or more byproducts is illustrated. In an example, at 502, the method 500 comprises separating the DGS into a low protein mixture and a high protein mixture. At 504, the method 500 comprises generating, from the low protein mixture, a biogas by an anaerobic digestion process. At 506, the method 500 comprises generating, from the high protein mixture, at least one of a vegetable oil from a vegetable oil separation process, a high protein animal feed from a separation process, and a microalgae biomass material from a microalgae production process.

Figure 6:
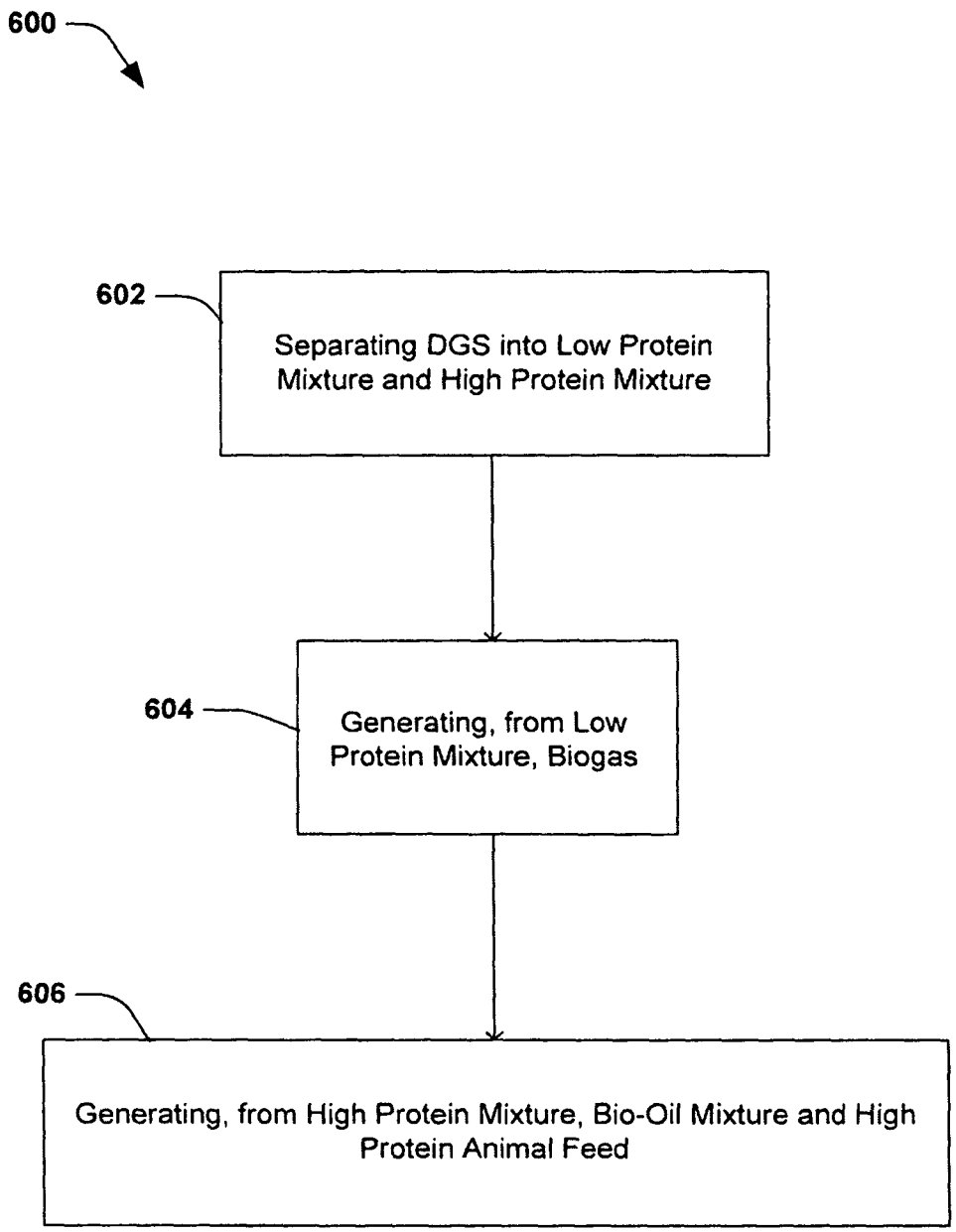
FIG. 6 illustrates an example method for treating DGS to produce one or more byproducts.

Referring to FIG. 6, an example Method 600 for treating DGS to produce one or more byproducts is illustrated. In an example, at 602, the method comprises separating the DGS into a low protein mixture and a high protein mixture. At 604, the method comprises generating, from the low protein mixture, a biogas. At 606, the method comprises generating, from the high protein mixture, a bio-oil mixture and a high protein animal feed.

A term such as "exemplary" is used herein to mean serving as an example, instance, illustration, etc., and not necessarily as advantageous. As used in this application, "or" is intended to mean an inclusive "or" rather than an exclusive "or". In addition, "a" and "an" as used in this application are generally be construed to mean "one or more" unless specified otherwise or clear from context to be directed to a singular form. Also, at least one of A and B and/or the like generally means A or B and/or both A and B. Furthermore, to the extent that "includes", "having", "has", "with", or variants thereof are used, such terms are intended to be inclusive in a manner similar to the term "comprising."

Many modifications may be made to the instant disclosure without departing from the scope or spirit of the claimed subject matter. Unless specified otherwise, "first," "second," or the like are not intended to imply a temporal aspect, a spatial aspect, an ordering, etc. Rather, such terms are merely used as identifiers, names, etc. for features, elements, items, etc. For example, a first set of information and a second set of information generally correspond to set of information A and set of information B or two different or two identical sets of information or the same set of information.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure. In addition, while a particular feature of the disclosure may have been disclosed with respect to only one of several implementations, such feature may be combined with one or more other features of the other implementations as may be desired and advantageous for any given or particular application.

What is claimed is:

1. A method for treating distiller's grains with solubles (DGS) to produce a high protein animal feed, the method comprising:
    treating the DGS with a steeping process that includes using a chemical; treating the DGS with a size reduction process; then separating the DGS into a low protein mixture and a high protein mixture; and
    generating, from the high protein mixture:
    a high protein animal feed from a separation process, wherein a percentage of protein content in the DGS is between about 25% and about 30%.

2. The method of claim 1, wherein the separating the DGS comprises at least one of centrifuging, filtration, or pressing.

3. The method of claim 1, further including adding liquid to the DGS to raise the moisture content to 80% or greater.

4. The method of claim 1, wherein the chemical used during the steeping comprises at least one of sodium hydroxide, potassium hydroxide, sodium sulfite, sodium sulfate, sodium metabisulfite, sodium bisulfite, and sodium dodecyl sulfate.

5. The method of claim 1, wherein a steeping time of the steeping step is between about 1 hour to about 48 hours at a temperature that is between about 25° Celsius to about 85° Celsius.

6. The method of claim 1, wherein the size reduction comprises at least one of disk milling, roller milling, hammer milling, colloid milling, and press milling.

7. The method of claim 1, wherein the separating comprises using a sieve having one or more pores with a pore size that is between about 0.1 micrometer and about 5 millimeters.

8. The method of claim 1, wherein the step of generating, from the high protein mixture, comprises separation by one of:
    centrifugation with a disk-stack centrifuge or a decanter; or
    static settling method.

9. The method of claim 1, wherein the step of generating, from the high protein mixture, comprises:
    heating the high protein mixture to a temperature that is between about 60° Celsius and about 100° Celsius;
    adding a demulsifier comprising at least one of alkali or alcohol; and adjusting a pH with at least one of an acid or an alkali.

10. A method for treating distiller's grains with solubles (DGS) to produce a high protein animal feed, the method comprising:
    treating the DGS with a steeping process that includes using an enzymatic solution;
    treating the DGS with a size reduction process; then
    separating the DGS into a low protein mixture and a high protein mixture; and
    generating, from the high protein mixture:

a high protein animal feed from a second separation process, wherein a percentage of protein content in the DGS is between about 25% and about 30%.

11. The method of claim 10, wherein the enzymatic solution used during the steeping comprises at least one of protease, carbohydrase, cellulase, hemicellulase, ligninase and pectinase.

* * * * *